US011998256B2

(12) United States Patent
Wahl et al.

(10) Patent No.: US 11,998,256 B2
(45) Date of Patent: *Jun. 4, 2024

(54) STERILE PACKAGING OF K-WIRE AND CAP

(71) Applicant: In2Bones USA, LLC, Memphis, TN (US)

(72) Inventors: Rebecca Hawkins Wahl, Escondido, CA (US); Alan G. Taylor, Memphis, TN (US)

(73) Assignee: In2Bones USA, LLC, Memphis, TN (US)

( * ) Notice: Subject to any disclaimer, the term of this patent is extended or adjusted under 35 U.S.C. 154(b) by 22 days.

This patent is subject to a terminal disclaimer.

(21) Appl. No.: 16/854,751

(22) Filed: Apr. 21, 2020

(65) Prior Publication Data

US 2020/0246052 A1    Aug. 6, 2020

Related U.S. Application Data

(62) Division of application No. 15/601,807, filed on May 22, 2017, now Pat. No. 10,660,683.

(Continued)

(51) Int. Cl.
*B65B 5/04* (2006.01)
*A61B 17/86* (2006.01)
(Continued)

(52) U.S. Cl.
CPC ............ *A61B 17/865* (2013.01); *A61B 50/30* (2016.02); *B65B 5/04* (2013.01); *B65D 77/0486* (2013.01);
(Continued)

(58) Field of Classification Search
CPC .......... B65B 5/04; B65B 5/06; B65B 7/2828; B65B 7/2835; B65B 2220/16;
(Continued)

(56) References Cited

U.S. PATENT DOCUMENTS 3,301,392 A   1/1967 Regan
3,602,218 A   8/1971 Riordan et al.
(Continued)

FOREIGN PATENT DOCUMENTS

DE    102015012898 A1 *  4/2017  ........... A61B 17/865

OTHER PUBLICATIONS

PCT International Search Report, PCT Application No. PCT/US17/34283, dated Oct. 20, 2017.

*Primary Examiner* — Stephen F. Gerrity
(74) *Attorney, Agent, or Firm* — Rutan & Tucker LLP; Hani Z. Sayed

(57) ABSTRACT

A method is provided for sterile packaging of a Kirschner wire (K-wire) and cap for shipping and storage, such that the K-wire and cap may be removed from the sterile packaging and used during a surgery. The method comprises sterile packaging the K-wire into a first container, sterile packaging the cap into a second container, and then bundling the first and second containers into a third container. In some embodiments, the first container may be comprised of a sterile interior environment within a double tube container, and the second container may be comprised of peel pouch configured to be unsealed during the surgery. In some embodiments, the K-wire and the cap may be placed together onto a mounting card that is then sterile packaged into a peel pouch that may be unsealed during the surgery.

4 Claims, 2 Drawing Sheets

Related U.S. Application Data

(60) Provisional application No. 62/342,281, filed on May 27, 2016.

(51) Int. Cl.
*A61B 50/30* (2016.01)
*B65B 5/06* (2006.01)
*B65D 77/04* (2006.01)
*A61B 17/84* (2006.01)
*A61B 50/00* (2016.01)

(52) U.S. Cl.
CPC ..... *A61B 17/848* (2013.01); *A61B 2050/0064* (2016.02); *A61B 50/3001* (2016.02); *A61B 2050/3006* (2016.02); *A61B 2050/3008* (2016.02); *B65B 5/06* (2013.01); *B65B 2220/16* (2013.01)

(58) Field of Classification Search
CPC ............... B65D 77/02; B65D 77/0486; B65D 77/0493; A61B 17/848; A61B 17/865; A61B 2050/0065; A61B 2050/3006; A61B 2050/3008; A61B 2050/314; A61B 2050/0064; A61B 50/3001; A61B 50/30
USPC .................................. 53/425, 449; 206/438
See application file for complete search history.

(56) References Cited

U.S. PATENT DOCUMENTS

| | | |
|---|---|---|
| 3,809,075 A | 5/1974 | Matles |
| 4,688,560 A | 8/1987 | Schultz |
| 5,330,476 A | 7/1994 | Hoit et al. |
| 6,622,864 B1 | 9/2003 | Debbs et al. |
| 8,246,561 B1 | 8/2012 | Agee et al. |
| 8,413,811 B1 | 4/2013 | Arendt |
| 2002/0029981 A1* | 3/2002 | Nigam ................... A61B 50/30 206/5.1 |
| 2006/0213794 A1* | 9/2006 | Foreman et al. ...... A61B 50/30 206/370 |
| 2011/0071572 A1* | 3/2011 | Sixto et al. .......... A61B 17/865 606/286 |
| 2012/0203290 A1* | 8/2012 | Warren et al. ....... A61B 17/864 606/86 A |
| 2013/0199947 A1* | 8/2013 | Tennican .................. B65B 5/00 206/216 |
| 2014/0042050 A1 | 2/2014 | Richart et al. |
| 2014/0277446 A1* | 9/2014 | Clifford et al. ......... A61B 17/56 623/13.12 |
| 2014/0371799 A1* | 12/2014 | Sixto et al. ............ A61B 50/30 606/281 |
| 2015/0313652 A1 | 11/2015 | Burckhardt et al. |
| 2016/0058510 A1* | 3/2016 | Blice et al. ............ A61B 50/30 206/210 |
| 2016/0059980 A1* | 3/2016 | Nemec .................... B65B 55/12 53/425 |
| 2016/0166350 A1* | 6/2016 | Burkhardt et al. .... A61B 50/30 206/572 |
| 2016/0228188 A1* | 8/2016 | Sweeney ............. A61B 50/30 |
| 2016/0278789 A1* | 9/2016 | Garvey et al. .......... B65B 55/12 |
| 2017/0095308 A1* | 4/2017 | Roesler et al. ........ A61B 50/30 |
| 2017/0166377 A1* | 6/2017 | Kaplan et al. ........ A61B 17/865 |
| 2017/0245902 A1* | 8/2017 | Hollis et al. ......... A61B 17/848 |

* cited by examiner

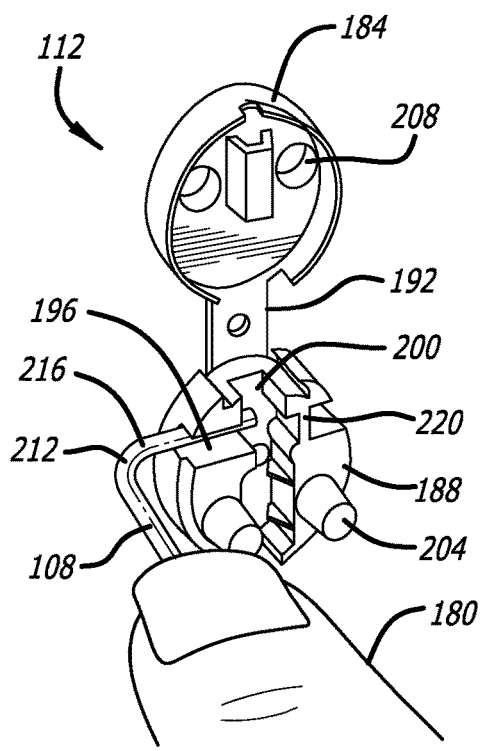
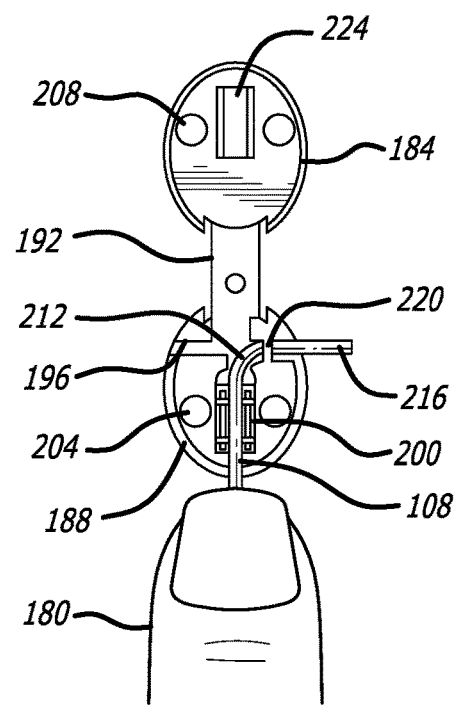
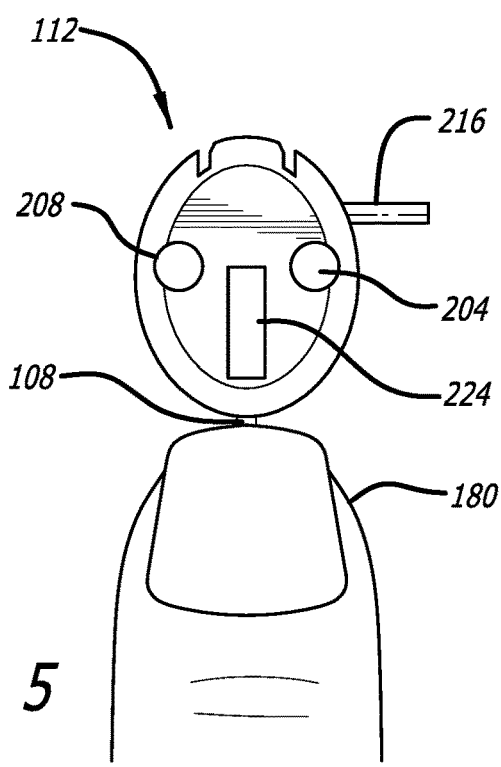
FIG. 3　　FIG. 4
FIG. 5

STERILE PACKAGING OF K-WIRE AND CAP

PRIORITY

This application is a divisional of U.S. patent application Ser. No. 15/601,807, filed May 22, 2017, which claims the benefit of and priority to U.S. Provisional Application No. 62/342,281, filed May 27, 2017, both entitled "Sterile Packaging Of K-Wire And Cap" and are incorporated in their entirety herein.

FIELD

The field of the present disclosure generally relates to containers. More particularly, the field of the invention relates to sterile packaging of K-wires and caps that is suitable for shipping, storage, and being opened during a surgery.

BACKGROUND

Kirschner wires, or K-wires, are sterilized, sharpened, smooth or threaded metal pins configured for a variety of medical, orthopedic, dental, and plastic surgical procedures, as well as various types of veterinary surgeries. K-wires are manufactured in different sizes and are used to hold bone fragments together, known as pin fixation, or to provide an anchor for skeletal traction. The K-wires are often driven into the bone through the skin, such as in percutaneous pin fixation, using a power or hand drill.

K-wires may be used for temporary fixation during some operations, and then removed after definitive fixation. Typically, the K-wires are removed four weeks post operation. K-wires are particularly suitable for definitive fixation of relatively small fracture fragments, such as wrist fractures and hand injuries. For example, in the case of treating a fracture of a distal phalanx, the K-wire may be introduced through a tip of the distal phalanx and advanced across the fracture toward the base of the distal phalanx. Often, the K-wire is cut such that an end of the K-wire protrudes through the skin from the tip of the finger. The end of the K-wire may either be bent to form a tight U-shaped configuration or a cap may be installed onto the end so as to prevent the K-wire catching on clothing, scratching the patient, and the like. As will be appreciated, leaving the K-wire protruding through the skin advantageously simplifies removal of the K-wire after definitive fixation.

Often times, K-wires and caps are shipped in a non-sterile state, and thus must be sterilized and stored before surgery. Further, additional apparatus and procedures may be required for sterilizing and storing of the K-wires and the caps. It is desirable, however, to ship a single K-wire that is coupled with a cap in sterile packaging, such that a surgeon may open the package and implant the K-wire and cap during surgery. What is needed, therefore, is a container that is amenable to various shipping methods, maintains sterility of enclosed K-wires and caps during shipping, and is simple to use before as well as during surgery.

SUMMARY

The present disclosure provides methods for sterile packaging a Kirschner wire (K-wire) and a cap for shipping, storage, and unpackaging during surgery. In some embodiments, the K-wire may be sterile packaged into a first container, the cap may be sterile packaged into a second container, and then the first and second containers may be bundled into a third container. In some embodiments, a first tube may be configured to receive the K-wire and the cap into a sterile interior environment of the first tube. A second tube may be configured to receive the first tube into an interior of the second tube. An interior closure may be engaged with a first end of the first tube and placed into contact with a support disposed within an enclosed end of the second tube. An exterior closure may be formed to receive a second end of the first tube and a threaded end of the second tube. In some embodiments, the first container may be comprised of a sterile interior environment within a double tube container, and the second container may be comprised of a peel pouch configured to be unsealed during the surgery. In some embodiments, the K-wire and the cap may be placed together onto a mounting card that is then sterile packaged into a peel pouch that may be unsealed during the surgery.

In an exemplary embodiment, a method for sterile packaging of a Kirschner wire (K-wire) and a cap for shipping and storage, comprising: coupling a K-wire and a cap that are suitable for fusing bone fractures; configuring a first tube to receive the K-wire and the cap into a sterile interior environment of the first tube; engaging an interior closure with a first end of the first tube; configuring a second tube comprising an enclosed end and a threaded end, the second tube having an inner diameter suitable to receive the first tube; and forming an exterior closure comprising an opening to receive a second end of the first tube and a threaded recess to engage with the threaded end, such that the interior closure contacts a support disposed within an enclosed end of the second tube.

In another exemplary embodiment, coupling comprises sourcing the K-wire and the cap so as to treat fractures of distal phalanges of fingers and toes. In another exemplary embodiment, sourcing further comprises selecting the K-wire, such that a trocar tip is disposed at opposite ends of the K-wire. In another exemplary embodiment, sourcing further comprises implementing the K-wire in any one of the following configurations: double trocar, single trocar, double diamond, single diamond, fully threaded, and partially threaded. In another exemplary embodiment, sourcing further comprises providing the cap in a configuration suitable for being folded closed onto the K-wire during a bone fusion surgery. In another exemplary embodiment, coupling further comprises mounting the cap in an open configuration onto an end of the K-wire.

In another exemplary embodiment, the method for sterile packaging further comprises configuring the sterile interior environment for containing at least one of the K-wire and the cap for fusing bones of the human body. In another exemplary embodiment, configuring the first tube and configuring the second tube comprises forming at least one of the first tube and the second tube of a rigid material, such as any of clear plastic, various polymer compounds, and the like. In another exemplary embodiment, configuring the first tube further comprises supporting the K-wire and the cap within the first tube by way of a flexible strip. In another exemplary embodiment, supporting comprises positioning the K-wire and the cap in substantially the middle of the first tube. In another exemplary embodiment, supporting further comprises configuring the flexible strip to facilitate removal of the K-wire and the cap from the sterile interior environment of the first tube. In another exemplary embodiment, configuring the flexible strip further comprises positioning an end of the flexible strip within the first tube, such that a practitioner may pull the flexible strip to remove the K-wire and the cap from the sterile interior environment of the first tube. In another exemplary embodiment, configuring the flexible strip further comprises configuring the flexible strip to loosen from the first tube upon being pulled at the end.

In an exemplary embodiment, a method for sterile packaging of a Kirschner wire (K-wire) and a cap for shipping and storage, such that the K-wire and the cap may be removed from the sterile packaging and used during a surgery, the method comprising: sterile packaging the K-wire into a first container; sterile packaging the cap into a second container; and bundling the first container and the second container into a third container that is suitable for shipping and storage.

In another exemplary embodiment, sterile packaging the K-wire comprises sealing the K-wire within a sterile interior environment of a first tube that is configured to be unsealed during the surgery. In another exemplary embodiment, sterile packaging the K-wire further comprises disposing the first tube within an interior of a second tube, such that the sterile interior environment is sealed from the interior of the second tube. In another exemplary embodiment, sterile packaging the cap comprises sealing the cap within a sterile interior environment of a peel pouch that is configured to be unsealed during the surgery. In another exemplary embodiment, sterile packaging the K-wire comprises configuring the first container in the form of a first tube having a sterile interior environment that is sealed from an interior of a second tube housing the first tube, such that the first tube may be removed from the second tube and unsealed during the surgery, wherein sterile packaging the cap comprises configuring the second container in the form of a peel pouch that may be unsealed during the surgery, and wherein bundling comprises configuring the third container to protect the first container and second container during shipping and storage. In another exemplary embodiment, bundling further comprises arranging the first container and the second container so as to create a surgery-specific bone fusion kit that may be accessed during the surgery for treating a bone fracture.

In an exemplary embodiment, a method for sterile packaging a Kirschner wire (K-wire) and a cap for shipping, storage, and unpackaging during surgery comprising: attaching the K-wire and the cap onto a sterile mounting card; and sealing the sterile mounting card into a sterile interior environment of a peel pouch that is configured to be unsealed during the surgery.

BRIEF DESCRIPTION OF THE DRAWINGS

The drawings refer to embodiments of the present disclosure in which:

FIG. 3 illustrates an exemplary embodiment of a K-wire and a cap after a surgeon has fused a fracture of a distal phalange of a finger;

FIG. 4 illustrates a centered configuration of the cap illustrated in FIG. 3 after the surgeon has aligned a longitudinal channel of the cap with the K-wire; and FIG. 5 illustrates a closed configuration of the cap illustrated in FIG. 4 after the surgeon has folded top and bottom portions of the cap so as to retain the K-wire within the longitudinal channel.

Figure 1:
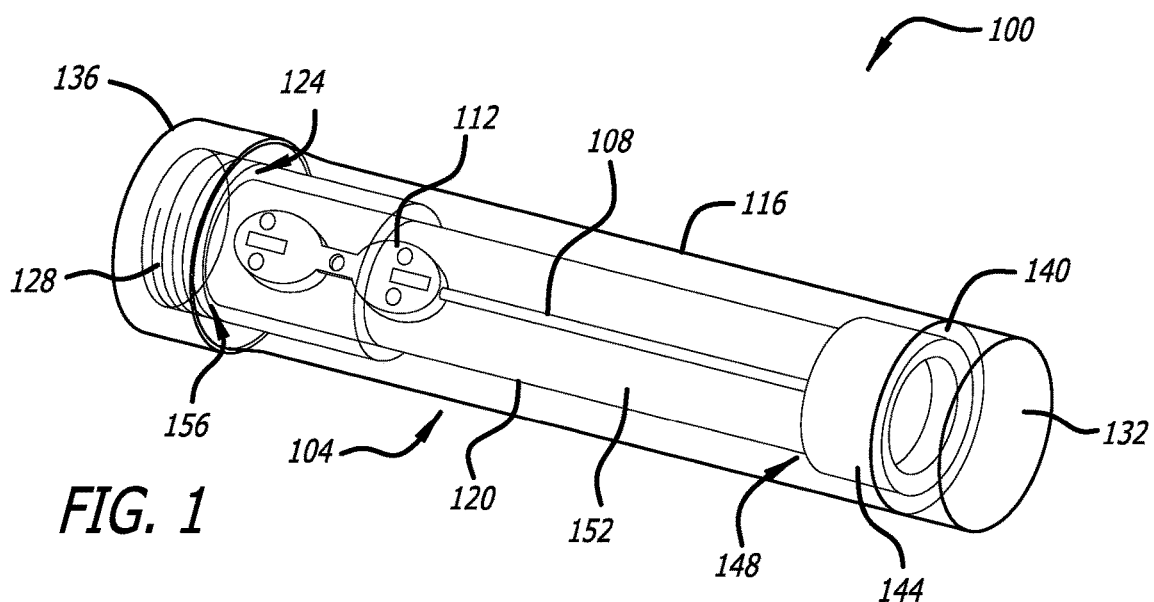
FIG. 1 illustrates an exemplary use environment comprised of a double tube container that is configured to store a K-wire and a cap, as well as other similar medical implements, in a sterile interior environment.

While the present disclosure is subject to various modifications and alternative forms, specific embodiments thereof have been shown by way of example in the drawings and will herein be described in detail. The invention should be understood to not be limited to the particular forms disclosed, but on the contrary, the intention is to cover all modifications, equivalents, and alternatives falling within the spirit and scope of the present disclosure.

DETAILED DESCRIPTION

In the following description, numerous specific details are set forth in order to provide a thorough understanding of the present disclosure. It will be apparent, however, to one of ordinary skill in the art that the invention disclosed herein may be practiced without these specific details. In other instances, specific numeric references such as "first tube," may be made. However, the specific numeric reference should not be interpreted as a literal sequential order but rather interpreted that the "first tube" is different than a "second tube." Thus, the specific details set forth are merely exemplary. The specific details may be varied from and still be contemplated to be within the spirit and scope of the present disclosure. The term "coupled" is defined as meaning connected either directly to the component or indirectly to the component through another component. Further, as used herein, the terms "about," "approximately," or "substantially" for any numerical values or ranges indicate a suitable dimensional tolerance that allows the part or collection of components to function for its intended purpose as described herein.

In general, the present disclosure describes a method for sterile packaging of a Kirschner wire (K-wire) and a cap for shipping and storage, such that the K-wire and the cap may be removed from the sterile packaging and used during a surgery. In one embodiment, the method comprises coupling a K-wire and a cap that are suitable for fusing bone fractures. A first tube is configured to receive the K-wire and cap into a sterile interior environment of the first tube. An interior closure is engaged with a first end of the first tube. A second tube is configured comprising an enclosed end and a threaded end, such that the second tube has an inner diameter suitable to receive the first tube. An exterior closure is formed comprising an opening to receive a second end of the first tube and a threaded recess to engage with the threaded end, such that the interior closure contacts a support disposed within an enclosed end of the second tube. In some embodiments, the first container may be comprised of a sterile interior environment within a double tube container, and the second container may be comprised of peel pouch configured to be unsealed during the surgery. In some embodiments, the K-wire and the cap may be placed together onto a mounting card that is then sterile packaged into a peel pouch that may be unsealed during the surgery.

FIG. 1 illustrates an exemplary use environment 100 comprised of a double tube container 104 that is configured to store a K-wire 108 and cap 112, as well as other similar medical implements, in a sterile environment. It is contemplated, however, that the K-wire 108 and the cap 112 may be sterile packaged in any suitable packaging that advantageously facilitates unpacking and using of the K-wire 108 and the cap 112 during surgery. To this end, it is further contemplated that the K-wire 108 and the cap 112 may be sterile packaged in any of various thermoformed medical trays, medical clamshell packaging, double polyethylene terephthalate glycol (PETG) trays, double Tyvek® pouches, blister trays, mounting cards, lidding and folding cartons, as well as any other suitable sterile package deemed appropriate.

The K-wire 108 and cap 112 illustrated in FIG. 1 generally are configured for fusing bones of the human body, and are particularly suitable for fusing fractures of distal phalanges of fingers and toes. The illustrated embodiment of the K-wire 108 generally is of the double trocar variety, having a trocar tip at opposite ends of the K-wire. In some embodiments, however, the K-wire 108 may be implemented in various configurations, including, but not necessarily limited to, double trocar, single trocar, double diamond, single diamond, as well as fully or partially threaded. The cap 112 is configured to be folded closed onto the K-wire 108 during a bone fusion surgery, as described herein. In the exemplary use environment 100 of FIG. 1, the cap 112 is coupled with an end of the K-wire 108 for storage in the double tube container 104.

The double tube container 104 generally comprises a first, exterior tube 116 configured to receive and retain a second, interior tube 120 within an opening 124 of the exterior tube 116, such that a sterile environment within at least the interior tube 120 may be maintained during shipping and storage of the double tube container 104. Preferably, the tubes 116, 120 are comprised of a rigid material, such as, by way of example, any of clear plastic, various polymer compounds, and the like.

The exterior tube 116 generally is an elongate hollow member comprising a threaded end 128 and an enclosed end 132. The threaded end 128 comprises the opening 124 and one or more circumferentially disposed threads on an exterior surface of the threaded end 128. The circumferentially disposed threads are configured to rotatably engage with similar threads disposed within a threaded recess of an exterior closure 136. As will be appreciated, inserting the interior tube 120 into the opening 124 and then rotatably engaging the threaded end 128 with the threaded recess of the closure 136 secures the interior tube 120 within the exterior tube 116. A textured surface may be disposed on an exterior surface of the exterior closure 136 so as to enable gripping and tightening of the closure 136 by way of a hand. A support 140 disposed at the enclosed end 132 within the opening 124 is configured to advantageously contact an interior closure 144 coupled with the interior tube 120 once the threaded end 128 is seated fully within the threaded recess of the exterior closure 136. The support 140 and the seating of the threaded end 128 within the exterior closure 136 cooperate to secure the interior tube 120 within the exterior tube 116.

The interior tube 120 comprises an elongate hollow member having the exterior closure 136 disposed at a first, proximal end and a threaded finish 148 disposed at a second, distal end. The threaded finish 148 comprises an opening into an interior 152 of the tube 120 and one or more threads circumferentially disposed on an exterior of the threaded finish 148. The threads are configured to rotatably engage with similar threads disposed within a threaded recess of the interior closure 144. As will be appreciated, rotatably engaging the threaded finish 148 and the interior closure 144 advantageously seals the interior 152 of the tube 120 by way of the interior closure 144, thereby preserving a sterile environment within the interior 152. A textured surface may be disposed on an exterior surface of the interior closure 144 so as to enable gripping the interior closure 144 by way of a hand.

In the embodiment illustrated in FIG. 1, the proximal end of the interior tube 120 is received within an opening 156 of the exterior closure 136 so as to advantageously maintain the sterile environment within the opening 152 of the tube 120. In some embodiments, threads may be disposed on an exterior surface of the proximal end of the interior tube 120 and configured to rotatably engage with similar threads within the opening 156. In such embodiments, the interior tube 120 may be threadably tightened into the opening 156. In some embodiments, the opening 156 may be configured to retain the proximal end of the interior tube 120 solely by way of friction. Thus, the proximal end of the tube 120 may be forcibly pressed into the opening 156. Further, in some embodiments any of various suitable adhesives may be included to retain the proximal end of the interior tube 120 within the opening 156. Moreover, although in the illustrated embodiment of FIG. 1, the interior tube 120 and the exterior closure 136 are separate components, in some embodiments the tube 120 and the closure 136 may comprise a single component. It should be understood, therefore, that any of various advantageous techniques for coupling the interior tube 120 with the exterior closure 136, suitable for maintaining the sterile environment within the opening 152, may be used without limitation, and without deviating beyond the spirit and scope of the present disclosure.

Based on the foregoing description, it should be recognized that the double tube container 104 is advantageously configured to preserve the sterility of the K-wire 108 and cap 112, or other surgical implements, during shipping and storage. During operation of the double tube container 104, a practitioner may insert the K-wire 108 and cap 112 into the opening 152 of the interior tube 120 and then rotatably engage the interior closure 144 with the threaded finish 148. Once the interior closure 144 is tightened onto the threaded finish 148 to a degree that is sufficient to maintain the sterile environment within the opening 152, the interior tube 120 may be inserted into the opening 124 so as to place the threaded recess of the exterior closure 136 in contact with the threaded end 128. Upon engaging and tightening the exterior closure 136 and the threaded end 128, the interior closure 144 advantageously contacts the support 140 within the enclosed end 132 of the exterior tube 116. Once the exterior closure 136 is sufficiently tightened onto the threaded end 128, the support 140 and the exterior closure 136 cooperate to support the interior tube 120 within the exterior tube 116.

Figure 2:
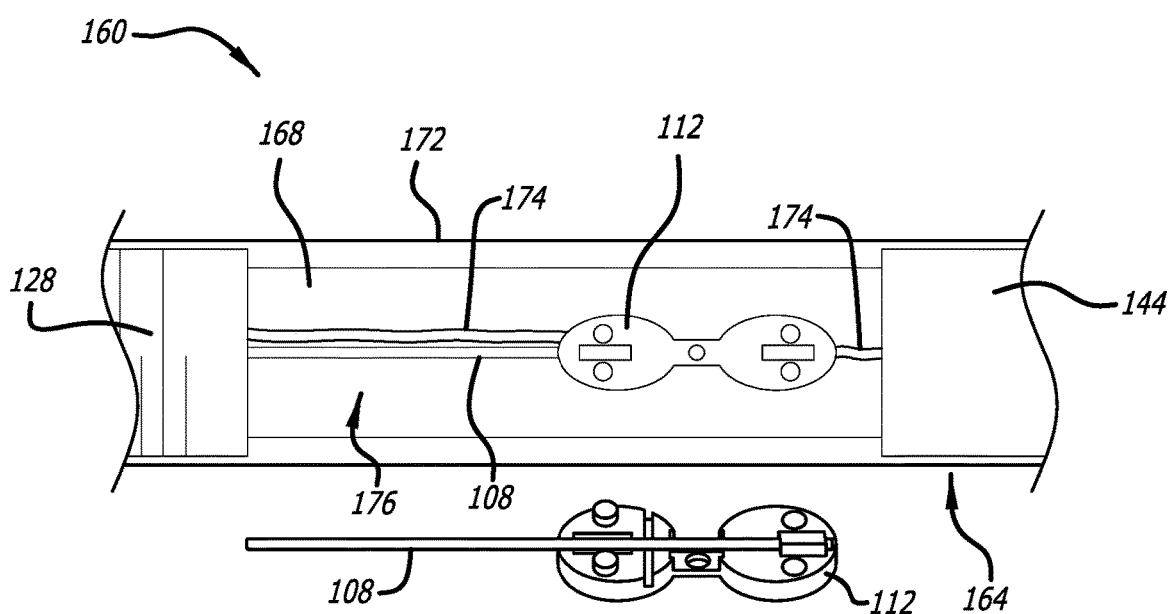
FIG. 2 illustrates an exemplary use environment wherein a K-wire and a cap are packaged in a sterile interior environment within a double tube container suitable for being shipped and stored.

FIG. 2 illustrates an exemplary use environment 160 wherein a K-wire 108 and a cap 112 are packaged in a sterile environment within a double tube container 164 in accordance with the present disclosure. The double tube container 164 is substantially similar to the double tube container 104, and thus is comprised of an interior tube 168 concentrically housed within an exterior tube 172. The K-wire 108 and cap 112 are stabilized within a sterile interior 176 of the interior tube 168, as described herein.

It is contemplated that, in some embodiments, the K-wire 108 and cap 112 may be supported by way of a flexible strip within the interior tube 168. As will be appreciated, the flexible strip may prevent damage to the K-wire 108 and cap 112, as well as to the interior tube 168, that may otherwise occur during shipping. Further, supporting the K-wire 108 and cap 112 substantially in the middle of the double tube container 164 facilitates directly viewing the K-wire and cap without a practitioner having to shake the K-wire and cap into view within the interior tube 168. It is envisioned that the flexible strip may be configured to position the K-wire 108 and cap 112 in any advantageous position within the interior tube 168, without limitation.

In some embodiments, the flexible strip may be configured to facilitate removal of the K-wire 108 and cap 112 from the double tube container 164. For example, an end of the flexible strip may be positioned within the interior tube 168, such that a practitioner may pull the flexible strip to remove the K-wire 108 and cap 112 free of the interior tube. In some embodiments, the flexible strip may be configured to loosen from the interior tube 168 upon being pulled at the end. It should be understood that the flexible strip may be configured and incorporated into the double tube container 164 without limitation, and without deviation beyond the spirit and scope of the present disclosure.

Moreover, it should be understood that the K-wire 108 and cap 112 are not limited to being sterile packaged within the double tube containers 104, 164, but rather the K-wire and cap may be sterile packaged in a wide variety of containers other than the double tube containers 104, 164, without limitation. For example, in some embodiments, the K-wire 108 may be sterile packaged within either of the double tube containers 104, 164, as described herein, and the cap 112 may be sterile packaged in a separate peel pouch. The double tube container and the peel pouch may then be bundled, or boxed, together so as to form a surgery-specific bone fusion kit. In some embodiments, the K-wire 108 and cap 112 may be placed together onto a mounting card and then sterile packaged into a peel pouch that may be unsealed during surgery.

Moreover, it should be understood that the K-wire 108 and the cap 112 need not be limited to being sterile packaged in the double tube containers 104, 164, but rather the K-wire 108 and the cap 112 may be sterile package in any suitable packaging that advantageously facilitates unpacking and using of the K-wire 108 and the cap 112 during surgery. As such, it is contemplated that the K-wire 108 and the cap 112 may be sterile packaged in any of various thermoformed medical trays, medical clamshell packaging, double polyethylene terephthalate glycol (PETG) trays, double Tyvek® pouches, blister trays, mounting cards, lidding and folding cartons, as well as any other suitable sterile package deemed appropriate.

FIGS. 3-5 illustrate an exemplary embodiment of a K-wire 108 and a cap 112 disposed in various configurations during fusing a fracture in a distal phalange of a finger 180. In the illustrated embodiment of FIGS. 3-5, the K-wire 108 generally is of the double trocar variety, having a trocar tip at opposite ends of the K-wire. It is contemplated that the K-wire 108 may have a length and a diameter suitable for fusing fractures of the distal phalanges of the figures and toes. In some embodiments, the length of the K-wire 108 may be substantially 4 inches and the diameter may range between substantially 0.035 inches and 0.062 inches, without limitation.

As best shown in FIG. 3, the cap 112 is comprised of a top portion 184 and a bottom portion 188 that share an intervening flexible strip 192. The bottom portion 188 is comprised of a lateral channel 196 and a longitudinal channel 200 that are configured to receive the K-wire 108. The flexible strip 192 is configured to allow the top portion 184 to be folded onto the bottom portion 188 so as to hold the K-wire 108 there between. One or more protrusions 204 disposed on the bottom portion 188 are configured to be fixedly received into corresponding openings 208 disposed in the top portion 184. As will be appreciated, upon pressing the top portion 184 onto the bottom portion 188, friction between the protrusions 204 and the openings 208 serves to keep the cap 112 in a closed configuration, as shown in FIG. 5.

FIG. 3 illustrates the K-wire 108 and cap 112 after a surgeon has fused the fracture of the distal phalange of the finger 180. The K-wire 108 is inserted across the fracture along the longitudinal axis of the finger 180 and extends through the skin. The surgeon has placed a bend 212 in the K-wire 108 and inserted a distal portion 216 of the K-wire into the lateral channel 196 of the cap 112. In the configuration shown in FIG. 3, the cap 112 is positioned perpendicularly to the longitudinal axis of the finger 180.

FIG. 4 illustrates a centered configuration of the cap 112 after the surgeon has advanced the distal portion 216 of the K-wire 180 through the later channel 196 so as to align the longitudinal channel 200 with the K-wire. The surgeon has rotated the cap 112 so as to seat the K-wire 108 within the longitudinal channel 200. A bridge 220 maintains the distal portion 216 seated within the lateral channel 196, as shown in FIG. 4. In some embodiments, the longitudinal channel 200 may be configured to fixedly retain the K-wire 108, such that the K-wire snaps into the longitudinal channel. In the configuration shown in FIG. 4, the top and bottom portions 184, 188 are aligned with the longitudinal axis of the finger 180 and are centered on the K-wire 108.

FIG. 5 illustrates a closed configuration of the cap 112 after the surgeon has folded the top portion 184 onto the bottom portion 188, such that the protrusions 204 are received into the openings 208. Upon pressing the top and bottom portions 184, 188 together, a longitudinal ridge 224 disposed in the top portion 184 is received into the longitudinal channel 200 of the bottom portion 188. The longitudinal ridge 224 and the longitudinal channel 200 cooperate to fixedly retain the K-wire 108 within the closed cap 112, as shown in FIG. 5. As will be appreciated by those skilled in the art, the closed cap 112 serves to protect the patient from the distal portion 216 of the K-wire extending from the finger 180, as well as provides a means for the surgeon to remove the K-wire 108 from the finger 180 after the fracture is sufficiently healed.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. To the extent there are variations of the invention, which are within the spirit of the disclosure or equivalent to the inventions found in the claims, it is the intent that this patent will cover those variations as well. Therefore, the present disclosure is to be understood as not limited by the specific embodiments described herein, but only by scope of the appended claims.

What is claimed is:

1. A method for sterile packaging of a Kirschner wire (K-wire) and a cap for shipping and storage, such that the K-wire and the cap may be removed from the sterile packaging and used during a surgery, the method comprising:

sterile packaging the K-wire and the cap within a container comprising an interior tube concentrically housed within an exterior tube;

the interior tube comprising a sterile interior environment;

the exterior tube configured to receive and retain the interior tube within an opening of the exterior tube, wherein the exterior tube comprises a threaded end and an enclosed end;

a support disposed at the enclosed end of the exterior tube;

a seating disposed at the threaded end of the exterior tube;

wherein rotatably engaging a threaded finish and an interior closure seals the interior;

providing a flexible strip within the interior tube;

wherein the K-wire and the cap are stabilized and supported by the flexible strip within the sterile interior environment of the interior tube;

wherein supporting the K-wire and the cap in the container facilitates direct viewing of the K-wire and cap;

the flexible strip configured to:
- position the K-wire and the cap within the interior tube; and
- facilitate removal of the K-wire and the cap from the interior tube; and wherein the support and the seating cooperate to secure the interior tube within the exterior tube.

2. The method of claim 1, wherein the sterile interior environment of the interior tube is configured to be unsealed during the surgery.

3. The method of claim 2, wherein the sterile interior environment is sealed from an interior of the exterior tube.

4. The method of claim 1, wherein the interior tube and the exterior tube are combined to create a surgery-specific bone fusion kit that may be accessed during the surgery for treating a bone fracture.

* * * * *